(12) United States Patent
Johnson et al.

(10) Patent No.: US 11,577,024 B2
(45) Date of Patent: Feb. 14, 2023

(54) DUAL LUMEN IV ADMINISTRATION SET

(71) Applicant: Bohnas Innovations LLC, Coeur d'Alene, ID (US)

(72) Inventors: Casey Johnson, Coeur d'Alene, ID (US); Doran Thomas, Post Falls, ID (US); Scott Johnson, Lake Charles, LA (US)

(73) Assignee: Bohnas Innovations LLC, Coeur d'Alene, ID (US)

( * ) Notice: Subject to any disclaimer, the term of this patent is extended or adjusted under 35 U.S.C. 154(b) by 132 days.

(21) Appl. No.: 16/869,009

(22) Filed: May 7, 2020

(65) Prior Publication Data

US 2020/0353164 A1 Nov. 12, 2020

Related U.S. Application Data

(60) Provisional application No. 62/971,435, filed on Feb. 7, 2020, provisional application No. 62/858,133, filed (Continued)

(51) Int. Cl.
*A61M 5/168* (2006.01)
*A61M 5/142* (2006.01)
(Continued)

(52) U.S. Cl.
CPC ........ *A61M 5/16804* (2013.01); *A61M 5/142* (2013.01); *A61M 5/1411* (2013.01);
(Continued)

(58) Field of Classification Search
CPC .......... A61M 39/20; A61M 2005/1403; A61M 2005/3117; A61M 2039/0081;
(Continued)

(56) References Cited

U.S. PATENT DOCUMENTS

| 4,219,021 A | 8/1980 | Fink |
| 4,585,435 A * | 4/1986 | Vaillancourt ......... A61M 5/158 D24/114 |

(Continued)

FOREIGN PATENT DOCUMENTS

| CN | 109045387 A | 12/2018 |
| DE | 102008052752 A1 | 4/2010 |

OTHER PUBLICATIONS

English Translation of CN109045387 A.
(Continued)

*Primary Examiner* — Brandy S Lee
(74) *Attorney, Agent, or Firm* — Lee & Hayes, P.C.

(57) ABSTRACT

A dual lumen IV administration set includes a first lumen having an inner diameter of a first value. A second lumen is paired with the first lumen, and the second lumen has an inner diameter of a second value that is greater than the first value. A flow merger merges flow output from a distal end of the first lumen and flow output from a distal end of the second lumen to form a single flow output in an exit lumen. An injection port intersects the first lumen, thereby providing injection access to flow therethrough, prior to merging with the flow output of the second lumen.

19 Claims, 8 Drawing Sheets

Related U.S. Application Data on Jun. 6, 2019, provisional application No. 62/849,742, filed on May 17, 2019, provisional application No. 62/845,769, filed on May 9, 2019.

(51) Int. Cl.
*A61M 5/14* (2006.01)
*A61M 39/22* (2006.01)
*A61M 5/32* (2006.01)
*A61M 5/31* (2006.01)
*A61M 39/24* (2006.01)

(52) U.S. Cl.
CPC .......... *A61M 5/3202* (2013.01); *A61M 39/22* (2013.01); *A61M 2005/1403* (2013.01); *A61M 2005/3117* (2013.01); *A61M 2039/248* (2013.01)

(58) Field of Classification Search
CPC ............ A61M 5/1411; A61M 5/16804; A61M 2039/248; A61M 39/22; A61M 39/285; A61M 5/142; A61M 5/1424; A61M 5/3202

See application file for complete search history.

(56) References Cited

U.S. PATENT DOCUMENTS

| | | |
|---|---|---|
| 5,259,587 A | 11/1993 | D'Alessio et al. |
| 5,658,260 A | 8/1997 | Desecki et al. |
| 2002/0077597 A1 | 6/2002 | Hart et al. |
| 2008/0154214 A1* | 6/2008 | Spohn ................ A61B 5/02141 604/247 |
| 2012/0016318 A1 | 1/2012 | Hoang et al. |
| 2014/0336610 A1 | 11/2014 | Michel et al. |
| 2018/0021511 A1* | 1/2018 | Fukuoka ............... A61M 5/158 604/256 |
| 2019/0070406 A1 | 3/2019 | Faden |

OTHER PUBLICATIONS

The PCT Search Report and Written Opinion dated Sep. 4, 2020 for PCT Application No. PCT/US20/32007, 9 pages.
The International Preliminary Report on Patentability for PCT Application No. PCT/US20/32007, dated Nov. 18, 2021, 8 pages.
Extended European Search Report dated Dec. 5, 2022 for European Patent Application No. 20802427.3, 8 pages.

* cited by examiner

DUAL LUMEN IV ADMINISTRATION SET

CROSS REFERENCE TO RELATED PATENT APPLICATIONS

This application claims priority to U.S. Provisional Patent Application No. 62/845,769, filed on May 9, 2019, entitled "IV Administration Set," and to U.S. Provisional Patent Application No. 62/849,742, filed on May 17, 2019, entitled "IV Administration Set," and to U.S. Provisional Patent Application No. 62/858,133, filed on Jun. 6, 2019, entitled "IV Administration Set," and to U.S. Provisional Patent Application No. 62/971,435, filed on Feb. 7, 2020, entitled "IV Administration Set," and incorporates each in its entirety by reference.

BACKGROUND

In the modern world, during medical procedures, particularly those involving anesthesia, it is common that saline and other health or anesthesiology-related drugs are administered to those undergoing surgery via an intravenous (IV) drip line. The techniques and variances of administration of the fluid and drugs (hereinafter referred to as "IV administration") are complex due to the many physical differences among individuals. Yet, the procedural steps taken to accommodate the differences tend to be fairly routine across various different types of procedures. That is, once the administrator knows what is needed for the individual, it is essentially a matter of monitoring the patient and administering the correct amounts or doses of fluid/drugs at the right time, using the proper procedural steps according to the situation.

However, over the many years since IV administration was conceived and implemented, the equipment available for such procedural IV administration has changed little. Of course, advancements have been made in material technology, anti-bacterial capabilities, and some structural enhancements of the apparatus used. Further, as the administrators' knowledge of how the body functions has increased, variances in the process of administration has improved as well. Nevertheless, even the most skilled administrators still make errors unintentionally, which errors might be minimized if the equipment was improved.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. Furthermore, the drawings may be considered as providing an approximate depiction of the relative sizes of the individual components within individual figures. However, the drawings are not to scale, and the relative sizes of the individual components, both within individual figures and between the different figures, may vary from what is depicted. In particular, some of the figures may depict components as a certain size or shape, while other figures may depict the same components on a larger scale or differently shaped for the sake of clarity.

DETAILED DESCRIPTION

Overview

This disclosure is directed to various embodiments of an IV administration set ("IV admin set," "IV set," or "set"). Depending on the environment or user, embodiments of an IV administration set according to this disclosure may be referred to in different situations as a procedural IV admin set, a run/stop IV admin set, a dual lumen IV admin set, or a flush IV admin set—each of which may be interchangeably used herein with respect to the IV administration set). More specifically, the subject matter herein is directed to a dual lumen IV set. An advantage of the embodiments of a dual lumen IV set described herein is that an administrator, who is an individual authorized to administer fluid and/or drugs via the dual lumen IV set, is able to administer a medication separately from the main fluid delivery lumen during a procedure. As such, the dual lumen IV set provides both patients and administrators greater efficiency, accuracy, speed, and precision in fluid and drug delivery without interference with or from the main fluid delivery lumen. Such benefits may allow IV administration to be more acutely tailored according to specific and instantaneous or unexpected needs of a patient's body. Other advantages provided by the dual lumen IV set may or may not be listed herein but may be recognized by professional administrators upon use of an embodiment of a dual lumen IV set.

Illustrative Embodiments of a Dual Lumen IV Administration Set

Figure 1:
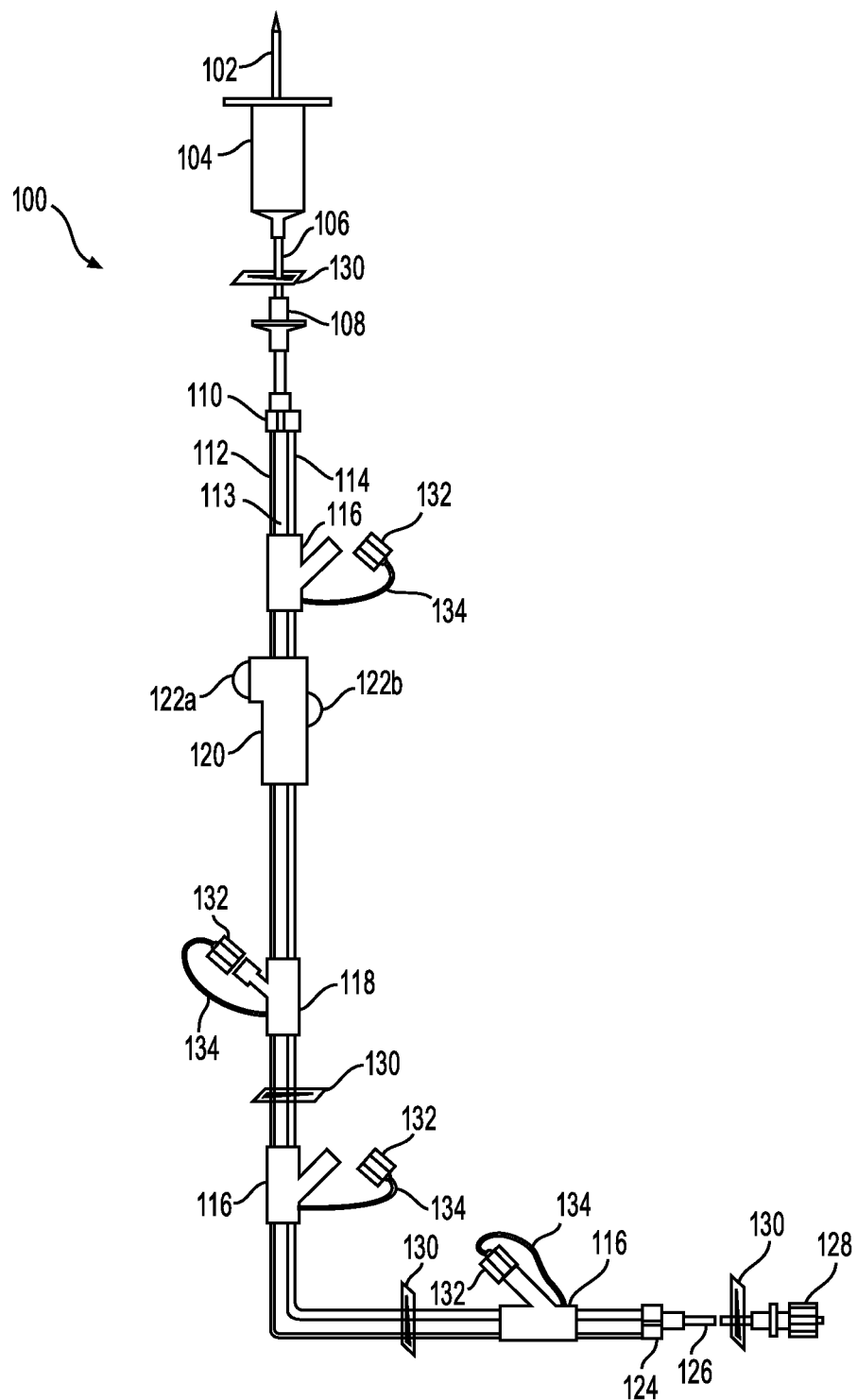
FIG. 1 illustrates a dual lumen procedural IV administration set according to an embodiment of this disclosure.

FIG. 1 depicts an embodiment of a dual lumen IV admin set 100. Starting with respect to the proximal end (i.e., for the sake of the description, the term proximal hereinafter refers to a portion of the dual lumen IV admin set 100 that is on the "fluid input" end, and thus the "fluid exit" end may be referred to as the distal end) of the dual lumen IV set 100 may include: a spike 102 and a drip chamber 104 for attachment to a fluid bag (not shown) to administer saline or other saline-like fluid according to the needs of the patient. The spike 102 may be the same or similar to known medical-industry spikes used to draw fluid from a saline bag. Additionally, the drip chamber 104 may be the same or similar to known drip chambers used in existing IV sets.

In an embodiment, a single input flow line 106 may extend from drip chamber 104. Due to distinctions of features (i.e., two lumens of different sizes) of the instant disclosure compared to a conventional single lumen IV admin set, the single input flow line 106 may be referred to as a macro-sized IV tube, which size may be comparable to the single lumen tubing of the conventional single lumen IV admin set. Moreover, in an embodiment not shown, but contemplated by the inventors, the input flow may be split into two separate input lines to directly meet the dual lumens of the dual lumen IV admin set 100. However, such an input flow arrangement may be more cumbersome to use. Accordingly, as described above and depicted, a single input flow line 106 may be implemented more conveniently.

Continuing with the description of the additional features in FIG. 1, the single input flow line 106 is connected to the drip chamber 104 on a proximal end and may be connected to a check valve 108 on the distal end. Check valve 108 may be included in the dual lumen IV admin set 100 to ensure fluid flows in only one direction, thereby preventing back flow. In general, the check valve 108 may be the same or similar to existing check valves.

Figure 2:
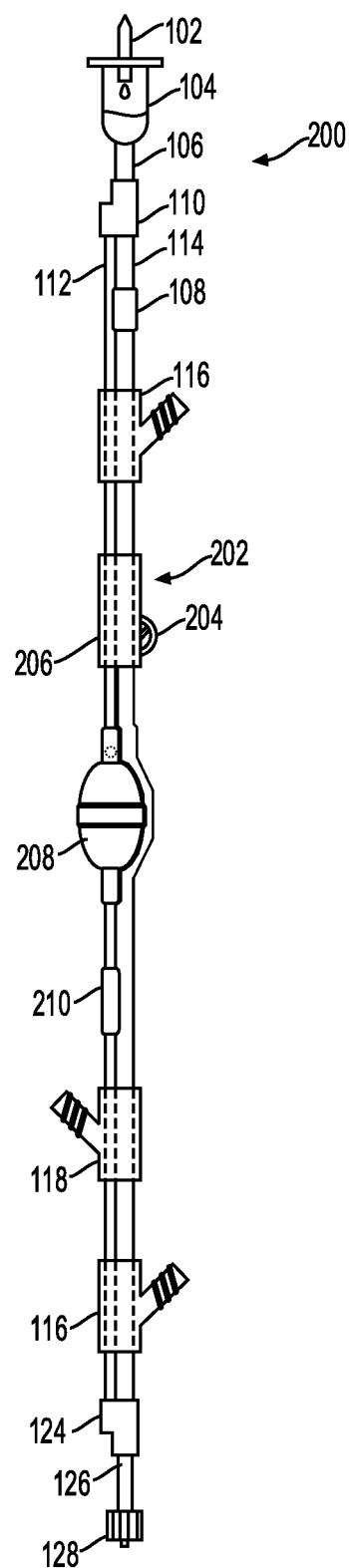
FIG. 2 illustrates another dual lumen procedural IV administration set according to an embodiment of this disclosure.

A flow splitter 110 is incorporated to facilitate directing fluid from the single input flow line 106 into both a first lumen 112 and a second lumen 114 of the dual lumen IV admin set 100. The first lumen 112 may also be referred to herein as a "micro lumen" to describe the relative size of the first lumen 112 with respect to the second lumen 114, or a "macro lumen." That is, as an inner diameter of first lumen 112 is smaller than an inner diameter of second lumen 114, first lumen 112 has a flow volume capacity that is less than the flow volume capacity of second lumen 114. Thus, it is not intended to mean that the lumen inner or outer diameter are necessarily of "micro" dimensions, though such is a possibility. Note, as depicted in FIG. 1, in an embodiment, the check valve 108 may be connected directly in line to the single input flow line 106. However, in an alternative embodiment as depicted in FIG. 2, the check valve (identified as 208) is positioned along the macro lumen after the flow is split.

In an embodiment, first lumen 112 and second lumen 114 may be joined via a thin webbing 113. Webbing 113 may be split as needed to separate first lumen 112 from second lumen 114. However, other embodiments, such as an embodiment shown in FIG. 2, may not include a webbing between first lumen 112 and second lumen 114, such that the two lumens (112, 114) may be manufactured as a unified body, which may be manually separated as needed, or may be joined after formation via various techniques to bond the lumens together. In an embodiment that includes webbing, other components of the dual lumen IV administration set may be altered from what is shown hereinafter to accommodate the webbing.

Dual lumen IV admin set 100 further includes one or more macro injection ports 116 intersecting the second lumen 114. Macro injection ports 116—the structure of which is described in more detail below—are points of administrator access into the second lumen 114 with first lumen 112 fluid flowthrough. The one or more macro injection ports 116 intersecting the second lumen 114 may be used to inject fluids/medications into the second lumen 114 according to current practices. The injection ports may include luer lock adapters or other suitable injection port adapter. Likewise, dual lumen IV admin set 100 further includes at least one micro injection port 118 intersecting the first lumen 112. Micro injection ports 118 are points of administrator access into the first lumen 112 with second lumen 114 fluid flowthrough, and the structure of the micro injection port 118 is also described in more detail below. Further, the at least one micro injection port 118 intersecting the first lumen 112 may be used to inject medication and fluids that are better suited for minimal dilution and/or more directed, faster injection. Accordingly, the at least one micro injection port 118 may be disposed nearer to the fluid output end of the dual lumen IV admin set 100 than to the fluid input end thereof.

In an embodiment, dual lumen IV admin set 100 may include a dual lumen clamping device 120. Dual lumen clamping device 120 may be configured to lockably secure and clamp both first lumen 112 and second lumen 114 independently, to regulate the volume of flow therethrough. For example, a first roller 122a may be positioned to roll in a grooved track, from a first end within dual lumen clamping device 120 to a second end thereof, and on a side securing first lumen 112, such that upon rolling first roller 122a, first lumen 112 is compressed between first roller 122a and an inner wall dividing first lumen 112 from second lumen 114. Likewise, a second roller 122b may be positioned to roll in a grooved track, from the first end within dual lumen clamping device 120 to the second end thereof, and on a side securing second lumen 114, such that upon rolling second roller 122b, second lumen 114 is compressed between second roller 122b and the inner wall.

Moreover, in an embodiment, first roller 122a may function as a mechanical timed locking clamp mechanism and second roller 122b may function as a lockable roller lock mechanism. That is, first roller 122a may include a track structure to act as a timed release, such that the clamping action on the lumen is maintained for a limited time before the clamp is self-released. Nevertheless, as described herein below, other clamps may be used in other embodiments, in which only one of the lumens is compressed or compressable to regulate flow of fluid therethrough, and/or where no timed locking clamp mechanism is included.

Prior to terminating in a single lumen flow to provide fluid to a patient via a single entry point, a flow merger 124 is incorporated in dual lumen IV admin set 100 to merge the flow of first lumen 112 and second lumen 114 back into a single exit lumen 126.

In an embodiment, dual lumen IV admin set 100 may incorporate a junction element 128, used to join exit lumen 126 with the extension tubing (not shown) that remains with the needle inserted in a patient. For example, junction element 128 may be a luer lock component, such as a male luer lock, though other suitable means of joining are possible. Additionally, one or more slide clamps 130 may be included to pinch off flow at a desired point, when equipped. Further, in an embodiment, one or more injection port caps 132 may be added to dual lumen IV admin set 100 to cover and clean the at least one macro injection port 116 and the at least one micro injection port 118. In an embodiment, injection port caps 132 may be tethered via a tether 134 to respective injection ports (116, 118), to assist in reducing bacteria introduction. Injection port caps 132 may include antibacterial and/or antiviral agents to clean respective injection ports (116, 118) before use and cover the same when not in use.

As seen in FIG. 2, in an alternative embodiment, a dual lumen IV admin set 200 may incorporate an alternative roller clamp 202 instead of dual lumen clamping device 120.

Figure 4C:
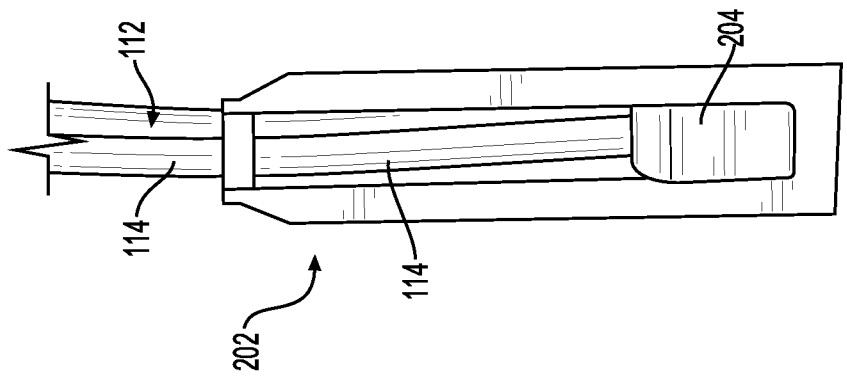
FIG. 4C illustrates a bottom view of the lumen roller clamp in FIG. 4A according to an embodiment of this disclosure.

Roller clamp 202 may clamp second lumen 114 via roller 204 to regulate flow therethrough, while allowing first lumen 112 to pass unobstructed. That is, in the embodiment of dual lumen IV admin set 200, roller clamp 202 does not have the means to clamp first lumen 112, and may include a bypass area 206 (shown in more detail in FIGS. 4A-4C) in which first lumen 112 may pass, while maintaining the ability to regulate the flow in second lumen 114 with a roller 204.

In addition, dual lumen IV admin set 200 may include a palpable flush pump 208. In an embodiment as shown, flush pump 208 may be a hand-squeezable flowthrough flush pump with a ball valve on one end, though it is contemplated that both ends of flush pump 208 may include a ball valve, in some instances. Generally, flush pump 208 may be incorporated into dual lumen IV admin set 200 by connecting a first end, which has a ball valve disposed therein, to be inline with first lumen 112 after flow splitter 110 and roller clamp 202.

Moreover, in an embodiment, a pressure valve 210 may be included in first lumen 112 beneath flush pump 208 to assist in preventing a continuous flow of the injected fluid from first lumen 112 prior to entering exit lumen 126 to pass into a patient.

Figure 3:
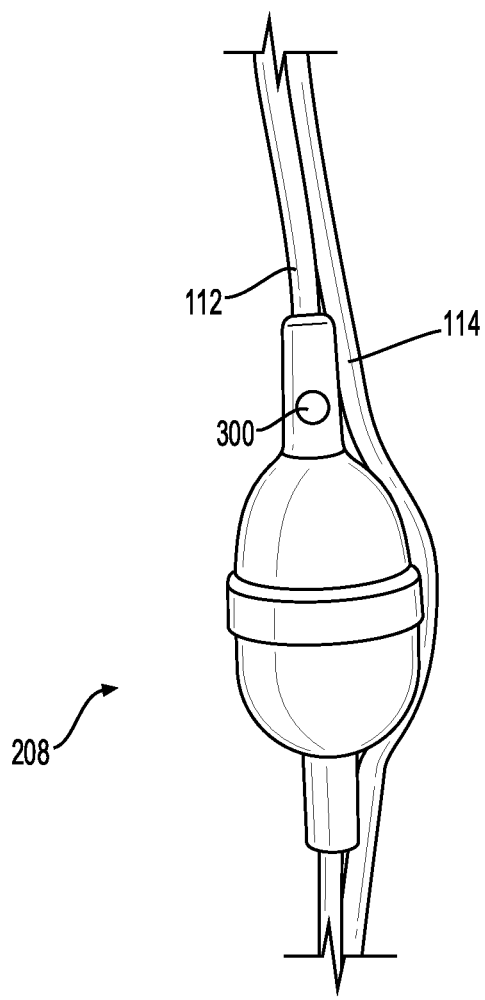
FIG. 3. illustrates an example flush pump according to an embodiment of this disclosure.

In an embodiment, as mentioned above, flush pump 208 may be a hand-actuated pump (see FIG. 3). Flush valve 208 may include a ball valve 300 at an upper end thereof to prevent backflow. Further, second lumen 114 may be adhered or otherwise affixed to an outer edge of ball valve 300 to avoid a loop that could potentially catch on structural features of patient beds, cabinets, worker clothing, etc. and could pull on the IV set 100. A size of flush valve 208 may vary depending on need. However, a 5 cc ball flush pump is contemplated. As indicated above, while flush pump 208 may be hand-actuated, it is also contemplated that a mechanized pump may be incorporated to assist in flushing the medication through first lumen 112.

Further, in an alternative embodiment, a ball valve may be included at each end of a flush pump (not shown), and the balls of the ball valves may be of a ferrite material. While squeezing, the ball of the top valve forces fluid foreword by overcoming the bottom valve and forcing the top valve up, thus closing off backflow. In contrast, while letting go of the ball at the top, a ball at the bottom of the pump may be sucked up closing the bottom valve off while filling. In an embodiment, a small magnet may be added above the bottom ball. The magnet may keep the lower ball bearing in the closed position preventing flow. Then, squeezing the pump may overcome the force of the magnet and forces enough fluid forward flushing the first lumen.

Figure 4B:
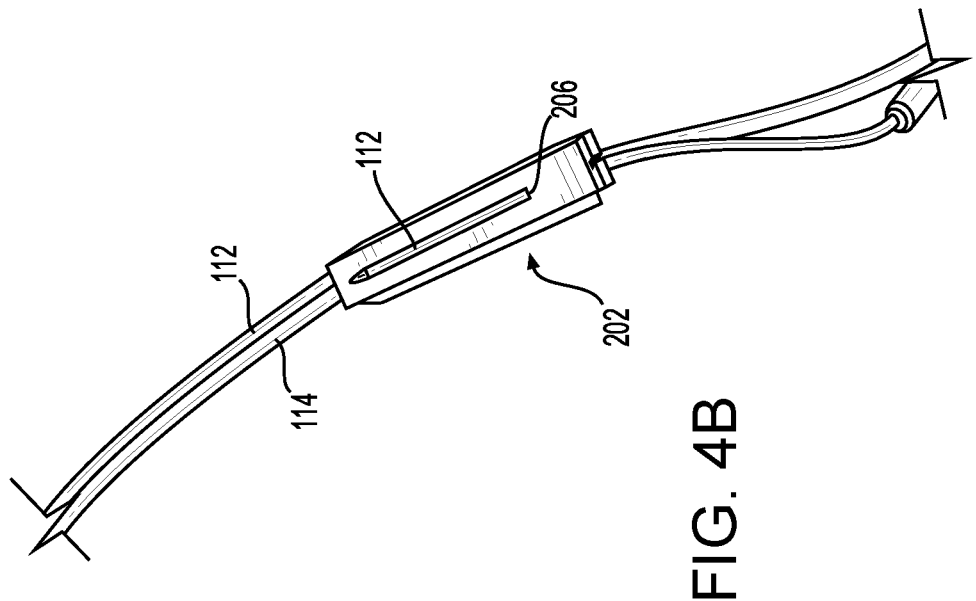
FIG. 4B illustrates a top view of the lumen roller clamp in FIG. 4A according to an embodiment of this disclosure.
Figure 4A:
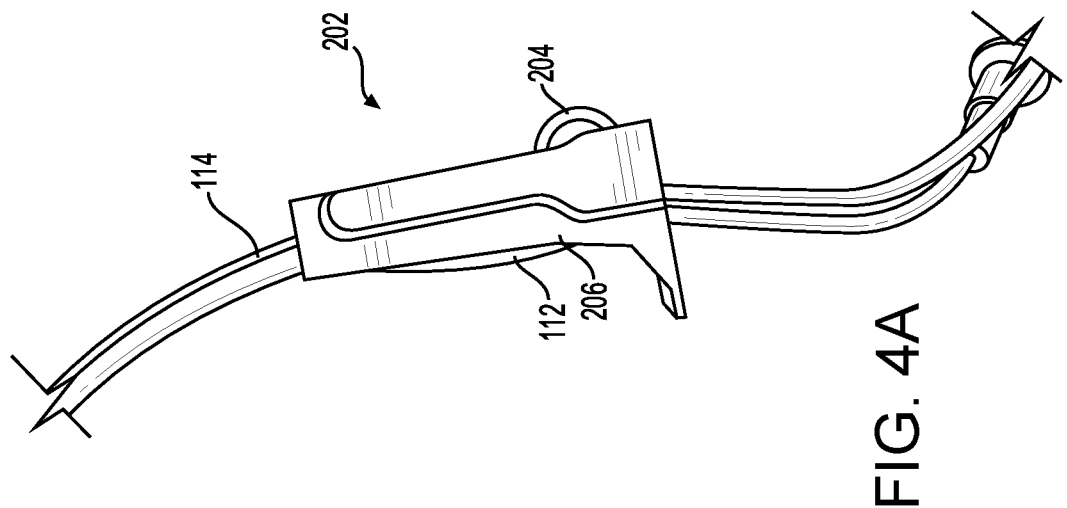
FIG. 4A illustrates a side view of a lumen roller clamp according to an embodiment of this disclosure.

In FIG. 4A, a side view of roller clamp 202 is shown. Roller 204 is shown at a side of roller clamp 202 opposite bypass area 206. In FIG. 4B, a top view of roller clamp 202 is shown, clearly depicting bypass area 206 in which first lumen 112 passes freely without clamping means to obstruct flow therethrough. Finally, in FIG. 4C, a bottom view of roller clamp 202 is shown, depicting roller 204 trapped within a track along side walls of roller clamp 202 and against second lumen 114.

Figure 5A:
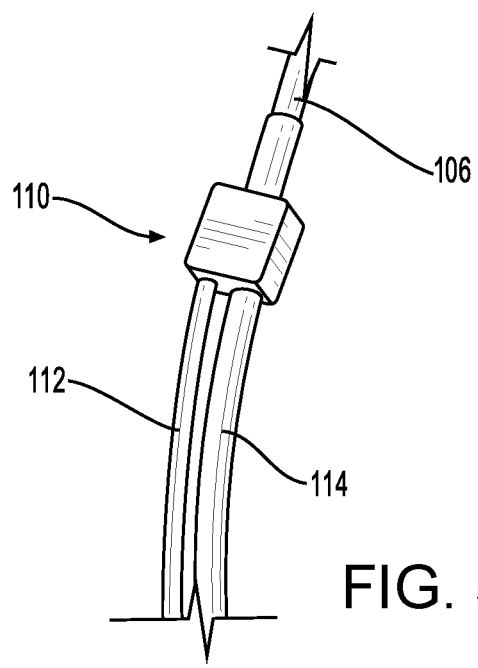
FIG. 5A illustrates a fluid input end portion of the procedural IV administration set of FIG. 2 according to an embodiment of this disclosure.
Figure 5B:
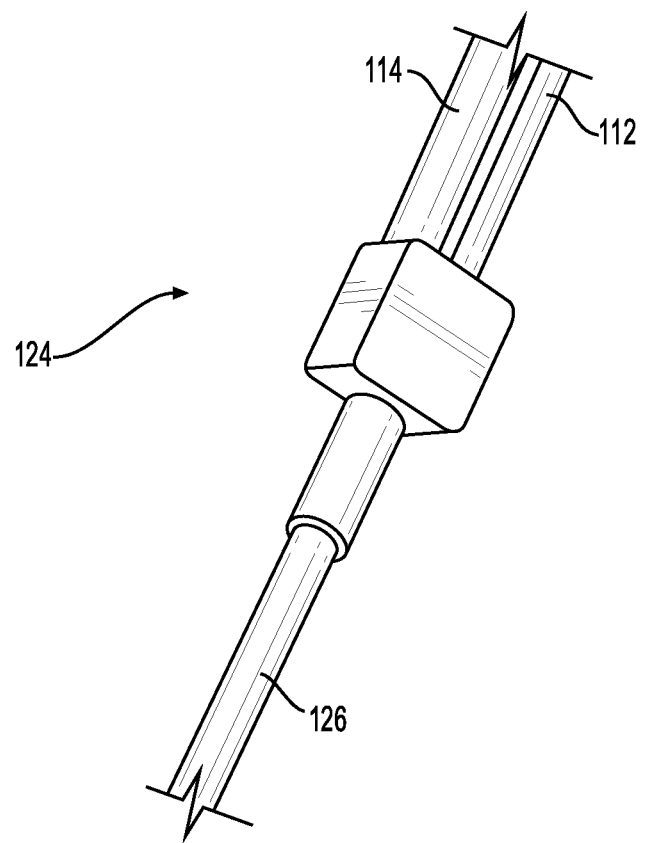
FIG. 5B illustrates an IV end portion of the procedural IV administration set of FIG. 2 according to an embodiment of this disclosure

FIGS. 5A and 5B depict the opposite components of flow splitter 110 in FIG. 5A and flow merger 124 in FIG. 5B. As explained above, flow splitter 110 divides the single input flow from single input flow line 106 into first lumen 112 and second lumen 114 via a block body structure configured to route the flow into the two exiting lumens (112, 114). While at the end of IV set 100, flow merger 124 reunites the separate flows of first lumen 112 and second lumen 114 into a single flow again at exit lumen 126.

Figure 6A:
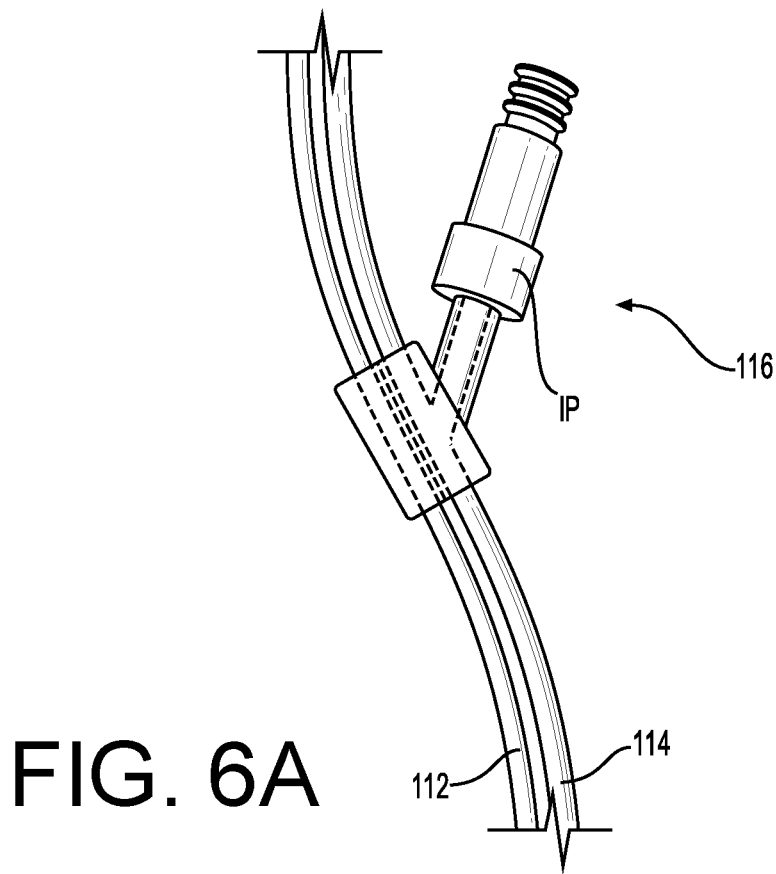
FIG. 6A illustrates a micro lumen injection port according to an embodiment of this disclosure.
Figure 6B:
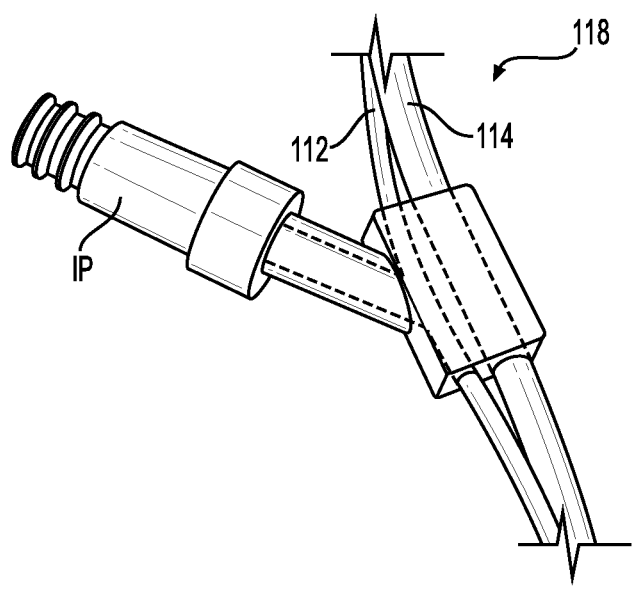
FIG. 6B illustrates a macro lumen injection port according to an embodiment of this disclosure.

The interior invisible structure of a macro injection port 116 is depicted in greater detail in FIG. 6A via the hashed lines within. That is, macro injection port 116 permits flow to continue uninterrupted in first lumen 112, while providing an injection port IP access into second lumen 114. Likewise, hashed lines within micro injection port 118, depicted in FIG. 6B, show the interior invisible structure. That is, micro injection port 118 permits flow to continue uninterrupted in second lumen 114, while providing an injection port IP access into first lumen 112.

Figure 7B:
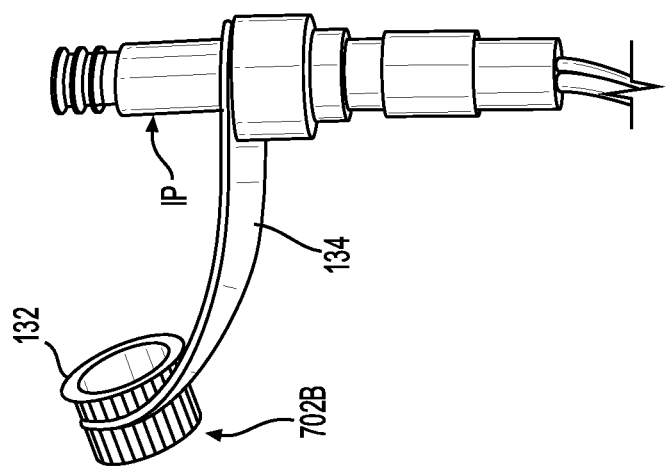
FIG. 7B illustrates an alternative injection port cleaning device according to an embodiment of this disclosure.
Figure 7A:
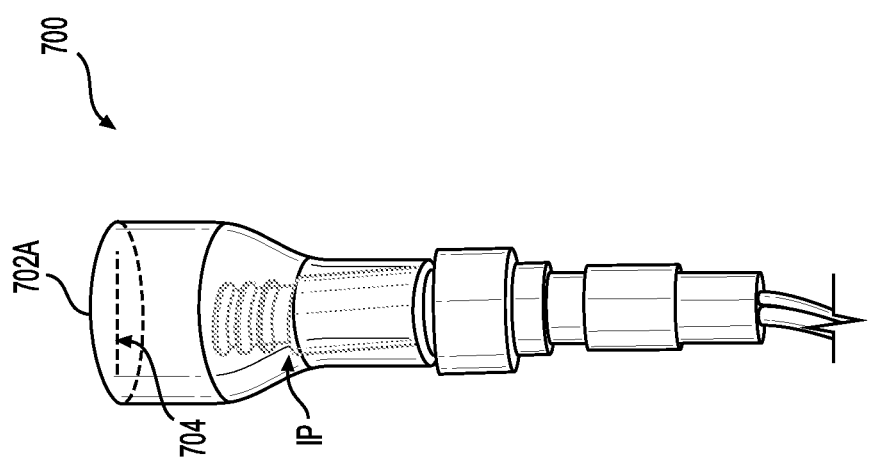
FIG. 7A illustrates an injection port cleaning device according to an embodiment of this disclosure.

FIG. 7A depicts an embodiment an injection port cap 700 used to clean the injection ports IP. Injection port cap 700 may include a rubberized or silicone-based, hollow, manipulable/movable cover, e.g., a resilient, but malleable nipple 702A. Nipple 702A may have a slit 704, via which the injection port IP may be exposed when nipple 702A is pulled to the side so that the injection port IP extends through slit 704, whereby injection access is available.

FIG. 7B illustrates an alternative embodiment of injection port cap 700 implementing a tethered cap 702B, which may be similar or the same as those depicted in FIG. 1 (injection port caps 132 as tethered via tether 134). Injection port cap 132 may be threaded on an inside thereof to clasp injection port IP securely. However, injection port cap 132 may alternatively be unthreaded, and merely fit around to be twisted and cleanse injection port IP. Tether 134 may be of flexible and durable material attached at a first end to the injection port IP and at a second, opposing end to cap 132, via which the injection port IP may be covered and/or cleaned.

As indicated above, the embodiments of caps may be attached in other ways, and may include a cleansing solution such as an antibacterial or antiviral solution, which may be in a liquid form and stored in an absorbent applicator within the cover or cap.

Illustrative Example of a Method of Using a Dual Lumen IV Administration Set

Figure 8:
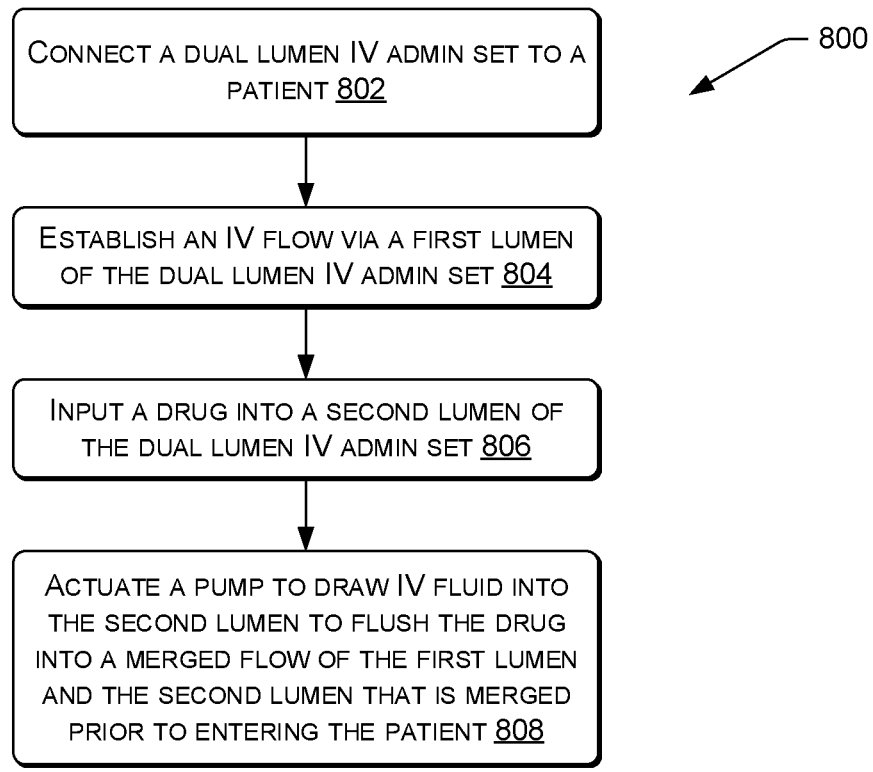
FIG. 8 illustrates a method of administering an IV fluid and/or medication to a patient via a dual lumen IV administration set.

Inasmuch as a dual lumen IV admin set has not been implemented prior to this disclosure, steps for use are described herein. For example, as shown in FIG. 8, a method 800 of administering an IV fluid and/or medication to a patient via a dual lumen IV administration set, as described herein above, may include connecting the dual lumen IV administration set to a patient 802 and establishing an IV fluid flow via a first lumen 804. Upon establishing the IV fluid flow, the administrator may input a medication, drug, or other solution (hereinafter referred to as "drug") needed into a second lumen 806 that runs parallel to the first lumen, and which second lumen has a flow that rejoins the flow of the first lumen prior to entering the patient. In connection with inputting the drug into the second lumen, the administrator may actuate a pump to draw IV fluid from the same source of IV fluid that is providing IV fluid to the first lumen 808, to flush the drug through the second lumen in a rapid manner and cause the drug to be administered at a point in the dual lumen IV administration set that is near an end thereof and prior to entering the patient.

CONCLUSION

Although several embodiments have been described in language specific to structural features and/or methodological acts, it is to be understood that the claims are not necessarily limited to the specific features or acts described. Rather, the specific features and acts are disclosed as illustrative forms of implementing the claimed subject matter.

What is claimed is:

1. A dual lumen IV administration set ("set") comprising:
a first lumen having an inner diameter of a first value;
a second lumen paired with the first lumen, the second lumen having an inner diameter of a second value that is greater than the first value;
a flow splitter to split input from a single flow input line into a first flow into the first lumen and a second flow into the second lumen;
a flush pump disposed inline with the first flow through the first lumen after the splitter, the flush pump configured to regulate a volume of the first flow via manual actuation of a valve disposed at a flow input end of the flush pump;
a flow merger to merge flow output from a distal end of the first lumen and flow output from a distal end of the second lumen to form a single flow output in an exit lumen; and
an injection port that intersects the first lumen prior to the flow merger, thereby providing injection access to flow therethrough, prior to merging with the flow output of the second lumen,
wherein the first lumen is coupled longitudinally at least in part to the second lumen between respective outer surfaces thereof.

2. The set according to claim 1, wherein the flush pump is manually actuated via hand squeezing the flush pump.

3. The set according to claim 2, wherein the flush pump is disposed above the injection port.

4. The set according to claim 2, wherein the flush pump includes a ball valve at a flow input end thereof.

5. The set according to claim 1, wherein the injection port is a first injection port, and
wherein the set further comprises at least one second injection port that intersects the second lumen, thereby providing injection access to the flow therethrough, prior to merging with the flow output of the first lumen.

6. The set according to claim 1, wherein the flow splitter and the flow merger are formed as respective individual components that are interchangeable such that by alternating an orientation of an individual component, the individual component is usable as either the flow splitter or the flow merger.

7. A dual lumen IV administration set ("set") comprising:
a first lumen;
a second lumen paired with the first lumen;
a flow splitter to split input from a single flow input line into a first flow into the first lumen and a second flow into the second lumen;
a squeezable flush pump disposed inline with the first flow through the first lumen after the splitter, the flush pump configured to regulate a volume of the first flow via manual actuation of a valve disposed at a flow input end of the flush pump;
a flow merger to merge flow output from a distal end of the first lumen and flow output from a distal end of the second lumen to form a single flow output in an exit lumen; and
an injection port that intersects the first lumen, thereby providing injection access to flow therethrough, prior to merging with the flow output of the second lumen.

8. The set according to claim 7, further comprising a check valve disposed on the second lumen after the flow splitter and before the flush pump,
wherein the flow splitter is formed as a singular individual component into which the single flow input line is inserted on a first end thereof and the first lumen and the second lumen are inserted on a second end thereof opposite the first end.

9. The set according to claim 8, wherein the flow splitter and the flow merger are identical components, disposed inversely in the set.

10. The set according to claim 8, further comprising a drip chamber having a spike, the drip chamber being connected to an end of the single input flow line.

11. The set according to claim 7, further comprising a lumen clamping device disposed to clamp the second lumen.

12. The set according to claim 11, wherein the lumen clamping device provides a bypass area where the first lumen passes freely.

13. The set according to claim 11, wherein the lumen clamping device includes a lockable roller to regulate flow through the second lumen.

14. The set according to claim 7, wherein the squeezable flush pump permits a user to palpate about 5 cc of fluid therethrough in a single palpation.

15. A dual lumen IV administration set ("set") comprising:
a first lumen;
a second lumen paired with the first lumen;
a flow splitter to split input from a single flow input line into a first flow into the first lumen and a second flow into the second lumen;
a flush pump disposed inline with the first flow through the first lumen after the splitter, the flush pump configured to regulate a volume of the first flow via manual actuation of a valve disposed at a flow input end of the flush pump;
a flow merger to merge flow output from a distal end of the first lumen and flow output from a distal end of the second lumen to form a single flow output in an exit lumen;
a lumen clamping device disposed to clamp the second lumen, the lumen clamping device being positioned before the flush pump; and
an injection port that intersects the first lumen, thereby providing injection access to flow therethrough, prior to merging with the flow output of the second lumen.

16. The set according to claim 15, wherein the flush pump is squeezable and is positioned between the lumen clamping device and the injection port.

17. The set according to claim 15, wherein the injection port includes a port cap that is tethered to the injection port.

18. The set according to claim 15, wherein the injection port includes a port cap that movably covers the injection port.

19. The set according to claim 18, wherein the port cap has a manipulable slit such that manual manipulation of the port cap causes the slit to open to allow an injection into the injection port, and upon termination of the manual manipulation, the slit closes to minimize a risk of bacteria infection via the injection port.

* * * * *